United States Patent [19]
Brachet

[11] 4,184,371
[45] Jan. 22, 1980

[54] APPARATUS FOR MEASURING THE DENSITY OF A BODY

[76] Inventor: Roland Brachet, Domaine d'Arnaga, Callian, France, 83810

[21] Appl. No.: 948,531

[22] Filed: Oct. 4, 1978

[30] Foreign Application Priority Data

Nov. 9, 1977 [FR] France .................................. 77 33770
Jul. 27, 1978 [FR] France .................................. 78 22229

[51] Int. Cl.² .......................... G01N 9/02; G01N 9/26
[52] U.S. Cl. ......................................... 73/433; 73/149
[58] Field of Search ..................... 73/32 R, 433–436, 73/149

[56] References Cited

U.S. PATENT DOCUMENTS

| | | | |
|---|---|---|---|
| 3,357,245 | 12/1967 | Wolfrum | 73/149 X |
| 3,769,834 | 11/1973 | Fletcher et al. | 73/149 |
| 4,095,473 | 6/1978 | Batchelor et al. | 73/433 |

FOREIGN PATENT DOCUMENTS

748729 12/1944 Fed. Rep. of Germany .
676130 11/1929 France .

*Primary Examiner*—John Petrakes
*Attorney, Agent, or Firm*—Sandler & Greenblum

[57] ABSTRACT

An apparatus for measuring the density of a body which comprises: a main chamber adapted to receive the body whose density is to be measured; an auxiliary chamber; a subsonic wave generator for subjecting both of said chambers, in phase, to amplitude variations of pressure so as to generate subsonic waves; a differential manometer arranged between each of said chambers; means for equalizing the subsonic pressures of said two chambers; measurement means driven by said means for equalizing said subsonic pressures; and, weighing means for weighing said body, said weighing means being arranged within said main chamber.

21 Claims, 7 Drawing Figures

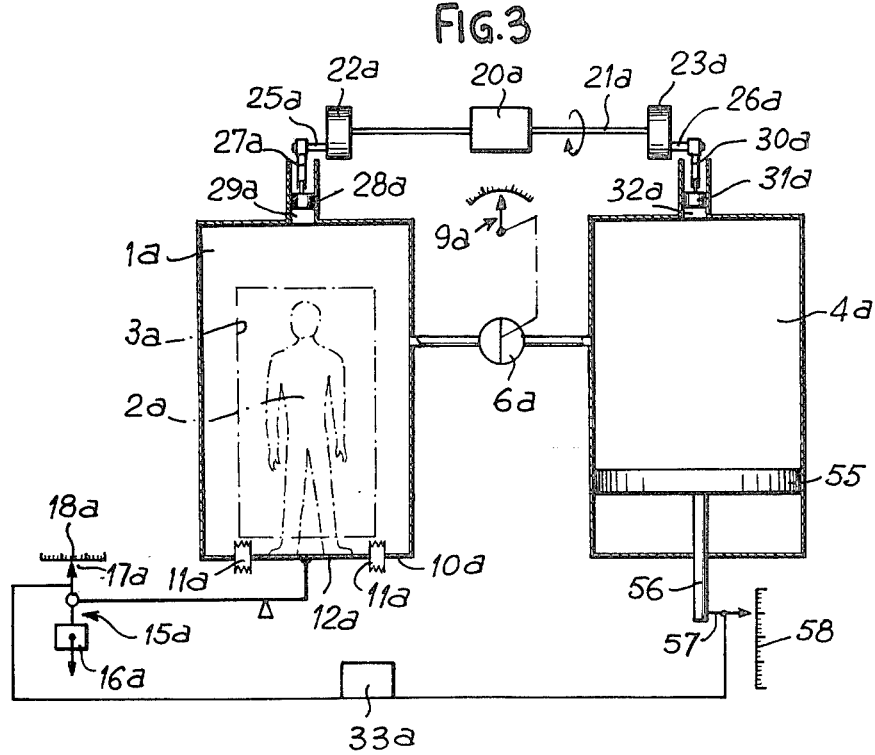
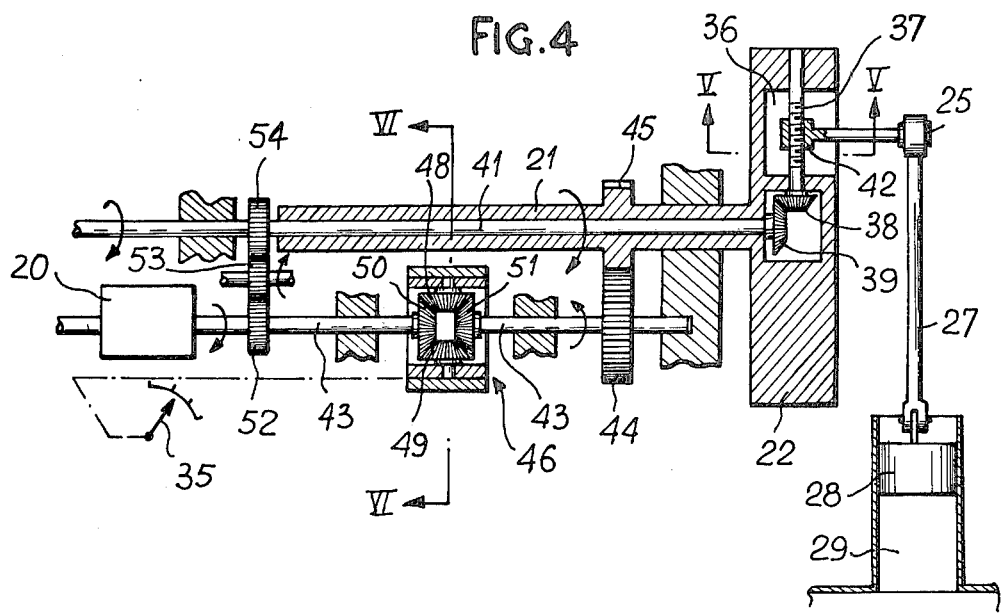

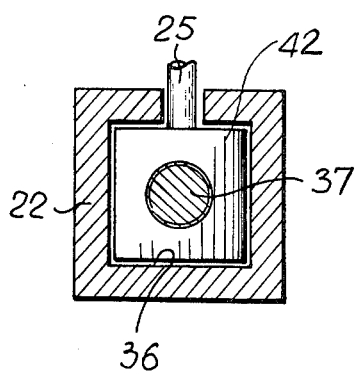
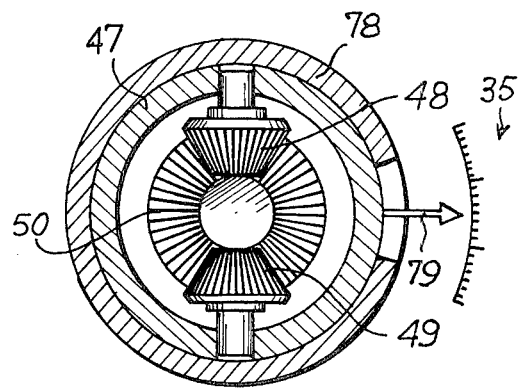
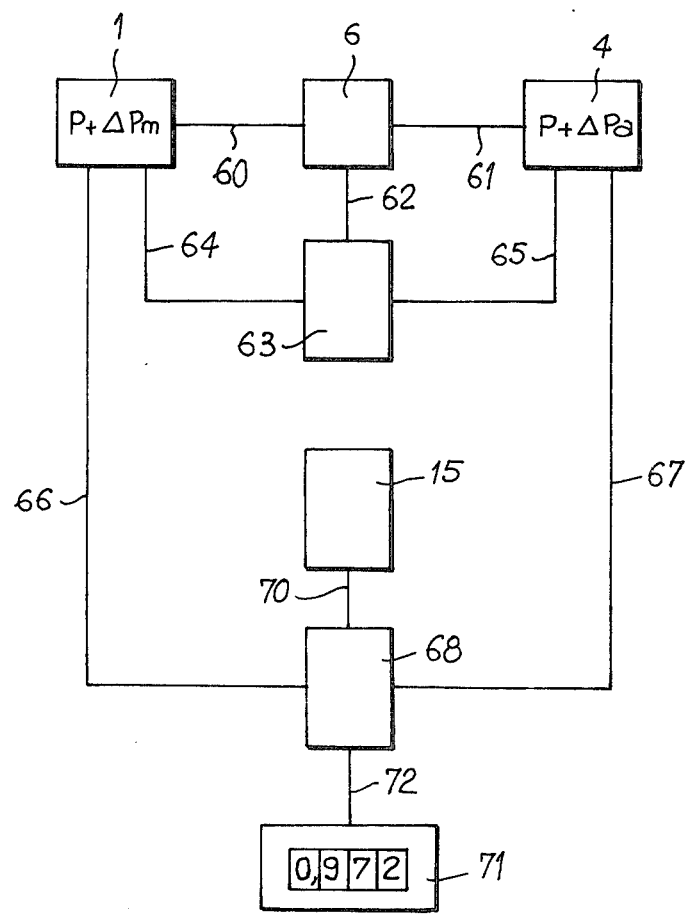

APPARATUS FOR MEASURING THE DENSITY OF A BODY

BACKGROUND OF THE INVENTION

1. Field of the Invention

The present invention relates to a device for measuring the density of a body, in particular a human body, under normal living conditions without being subjected to any restrictions.

2. Description of the Prior Art

As used throughout the application, the term "density" is taken to refer to the average density of an organism at a given moment under given physiological conditions, e.g., before or after inhalation, the consumption of a meal, etc.

The prior art in this domain does not easily lend itself to definition. It has been stated by some physicians that knowledge of body density is useful in principle, both for physiological research and pathological characterization, however, the devices developed for such measurements have encountered various difficulties until this time.

Direct measurement by the displacement of an equivalent volume of water not only calls for an artificial respiratory device but also entails discomfort caused to the patient by the total immersion which is necessary. Indirect measurement by the combination of two independent measurements, that of the volume of the human body and that of its mass, have likewise hitherto proven impractical for reasons which will now be set forth.

Known techniques for measuring the volume of a body comprise the steps of placing the body in an enclosure filled with a certain gas at a given pressure and of "treating" this gas by one of the following processes:

(1) Exciting a resonant acoustic frequency, which is a function of the residual volume between the enclosure and the body. This phenomena, adequately described by HELMHOLTZ, after whom such "resonators" have been named, is expressed by a relatively complex law in which the volume and the frequency are interdependent while at the same time being a function of additional variables.

(2) Subjecting the residual volume between a chamber and the body within the chamber to a known variation of volume and measuring the resulting pressure variation. The method may be "static", i.e., based on the use of one single compression level, or "dynamic", i.e., with compression varying according to an alternating function.

The above techniques are not as simple as they may appear. The possibilities offered by the first method are seriously limited by the necessity of preventing leaks from the chambers and also by the temperature fluctuations which occur. The problems of "propagation", i.e., the finite speed at which a disturbance in a gas is propagated, set limits to the possibilities offered by the second method.

Thus, whether the static or the dynamic method is adopted, the difference between isothermic and adiabactic compression has to be taken into account and the the coefficient $\gamma$, equal to the quotient obtained from the two specific heats, that prevailing at constant pressure and that prevailing at a constant volume, must be taken into account. Furthermore, it is necessary to accurately determine not only the volumetric variation creating the phenomenon, but also the pressure prevailing in the enclosure which plays a direct role in the measurement.

Whether the resonance method or the volume-pressure sounding method is used, the living organism being studied must not be injured or disturbed, a condition which neither of the techniques has been able to satisfy thus far.

Finally, whatever the volumetric measuring method adopted, the weight of the subject must still be determined as well. When independently measuring weight in order to determine density by simple division, a number of problems are encountered. There are, therefore, problems of not only convenience but also of rapidity, particularly in the case of physiological experiments, in which the weight of the subject may vary in the course of one and the same cycle of measurements and in which it must be possible for the density (varying as a result of the consumption of liquids or solids, urination, etc.) to be followed continuously.

SUMMARY OF THE INVENTION

It is, therefore, an object of the invention to provide a device which may be used to measure the density of a body by a technique which does not necessitate a knowledge of the ambient pressure to which the body is exposed, or of the compressibility coefficient $\gamma$ of the fluid gas with which the chamber is filled.

It is a further object of the invention to provide an apparatus which operates on simple physical principles in which measurement is effected by the "zero" technique and in which only geometrical magnitudes which are known with a high degree of accuracy play any role.

Yet another object of the invention comprises providing an apparatus in which the weight of the subject is directly measured thus permitting direct evaluation of the density of the body.

These and other objects of the invention are fulfilled by an apparatus for measuring the density of a body which comprises: a main chamber adapted to receive the body whose density is to be measured; an auxiliary chamber; a subsonic wave generator for subjecting both of the chambers, in phase, to amplitude variations of pressures, so as to generate subsonic waves; a differential manometer arranged between each of said chambers; means for equalizing the subsonic pressures of said two chambers; measurement means driven by said means for equalizing said subsonic pressures; and, weighing means for weighing said body, said weighing means being arranged within said main chamber.

The apparatus of the invention further comprises means connected to the measurement means and to the weighing means for receiving data from each of these means so as to calculate the density of the body. The subsonic wave generator preferably generates subsonic waves in each of the chambers by volumetric displacement and the means for modifying the amplitude of the volumetric displacement which generates said subsonic waves may be arranged in either the main or auxiliary chamber. Alternatively, the means for equalizing the subsonic pressure may comprise means for varying the volume of the auxiliary chamber such as by providing the auxiliary chamber with a base reciprocable piston adapted to vary the volume of this chamber.

In the first two embodiments of the invention, where the means for modifying the amplitude of the volumetric displacement are used, the apparatus comprises two assemblies, both of which are driven by a motor. Such an apparatus comprises a shaft connected to the motor; a piston arranged within a cylinder communicating with each of said chambers so as to reciprocate in the chamber; a crankshaft connected to the piston; and, means for varying the amplitude of reciprocation by the piston reciprocating in the cylinder communicating with either the main chamber or the auxiliary chamber, depending on which of the first two embodiments is selected. A plate is arranged between the crankshaft and a hollow shaft operatively connected to said shaft so as to be driven thereby. An inner shaft is inserted within the hollow shaft, this inner shaft ending in a first angle pinion. The apparatus may further comprise a threaded rod radially arranged within the plate, this threaded rod ending in a second angle pinion arranged to engage the first angle pinion at a right angle. The crankshaft ends in a nut which threadably engages the threaded rod and a connecting rod is arranged between the crankshaft and the piston. The connecting rod is adapted to raise and lower the piston as the plate is rotated by the hollow shaft.

A differential is operatively associated with both the hollow and inner shafts. The differential comprises a guide, a planetary gear carrier within the guide; two first planetary gears radially arranged within the planetary gear carrier; a differential shaft which extends out of the differential and comprises a first pinion adapted to drive the hollow shaft and a second pinion adapted to drive the inner shaft on opposite sides of the differential, said first and second pinions being adapted to be rotated in opposite directions when the side of the differential comprising the second pinion is driven by the shaft coming from said motor thus causing the hollow shaft and the inner shaft to rotate at substantially the same rotational velocity.

The measuring means is operatively connected to the differential and may, in the first two embodiments, comprise a manipulable element attached to the planetary gear carrier such that both of the opposite sides of the differential shaft are driven in the same direction, as the manipulable element is rotatably moved, which causes the hollow shaft and the inner shaft to rotate at different velocities relative to one another, which in turn causes the second angle pinion to rotate the threaded rod, thus altering the radial position of the crankshaft as the nut moves along the threaded rod.

As will be explained in further detail, the apparatus may additionally comprise a discriminator operatively connected to the differential manometer for processing information received from the manometer and then formulating instructions for equilibrating the subsonic pressures between each of the chambers based upon the information received. In addition to the discriminator, a computer means may be used for receiving data from the measurement means and the weighing means as well as for calculating the density of the body based upon the information received. The computer means may comprise display means for displaying the density calculated by the computer.

The apparatus of the invention has the further advantage that the measuring chamber need not be absolutely hermetically sealed and that thermal phenomena do not falsify the measured results. Furthermore, the density of the body is measured in a "normal" atmosphere in which the body, in the case of human subject, may breath, speak, and move without restrictions significantly greater than those which might exist in a telephone booth, for example. Additionally, the overall time constant of the measurement operation is sufficiently short so as to enable physiological phenomena such as a respiratory movement to be followed and measured.

BRIEF DESCRIPTION OF THE DRAWINGS

As shown by way of example in the accompanying drawings:

FIG. 3 is a schematic view of a third embodiment of the invention;

FIG. 4 is a schematic sectional diagram of means for varying the stroke of the piston either in the main chamber or in the auxiliary chamber;

FIG. 5 is a sectional view along line V—V of FIG. 4;

FIG. 6 is a sectional view along line VI—VI of FIG. 4; and

FIG. 7 is a block diagram of a device in accordance with the invention.

DESCRIPTION OF PREFERRED EMBODIMENTS

The apparatus of the invention comprises a main chamber designed to accomodate the patient or other body whose density is to be measured as well as an auxiliary chamber. Also provided are a subsonic wave generator which subjects the two chambers synchronously to pressures and depressions, and a differential pressure guage interposed between the two chambers. Additionally, means for equalizing the subsonic pressures between the two chambers together with measuring devices controlled by the said means for equalizing the subsonic pressure also form part of the device. Devices serving to measure the weight of the subject are situated in the main chamber. Finally, the apparatus comprises means for processing the density as a function of the data obtained by the means for equalizing the subsonic pressure and means for measuring the weight of the subject.

The acoustic phenomena utilized are subsonic and are in no way felt by the subject, partially as a result of their frequency, which is on the order of 5 Hz, and partially because of their low amplitude. A subsonic microphone such as the differential manometer between the two chambers is sensitive to pressures of a thousandth of a millibar, while the acoustic pressure prevailing around the subject will not be in excess of about a millibar.

Figure 1:
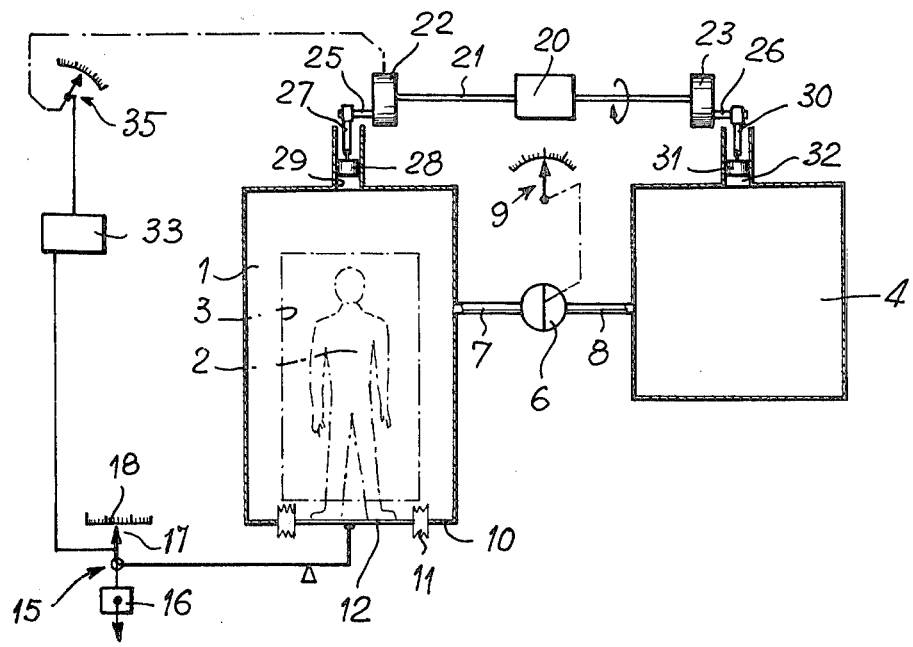
FIG. 1 is a schematic view of a first embodiment of the device according to the invention.
Figure 2:
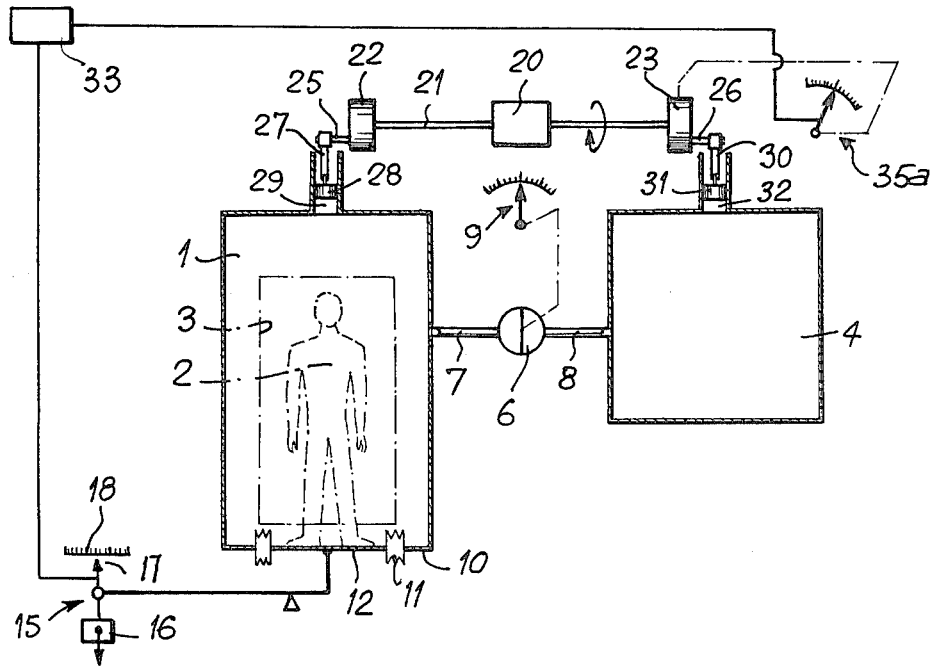
FIG. 2 is a schematic view of a second embodiment of the invention.

FIGS. 1, 2, and 3 show embodiments of the apparatus on an exaggerated scale for purposes of illustration. In this way all the elements utilized in the apparatus to which the invention relates and the way in which they are interrelated may be adequately described.

The device shown in FIG. 1 comprises a main chamber 1 designed to accomodate a human body 2 whose density is to be ascertained. The chamber includes an access door 3, shown in dashed lines. The chamber is normally in communication with the surrounding air; the door only being closed at the moment when the measuring operation is to be performed.

The device includes an auxiliary chamber 4 and, between the two chambers, a differential manometer gauge 6 connected to the main chamber by a tube 7 and to the auxiliary chamber by a tube 8. This differential pressure gauge controls a display device 9 which continuously shows the pressure difference prevailing between the two chambers.

The base 10 of the main chamber 1 possesses an independent section 12 connected by flexible joints 11 to the base 10.

The independent section 12 constitutes the platform of a weighing device 15 shown schematically comprising moveable counter weight 16 and an indicator needle 17 moveable along a graduated scale 18.

The shaft 21 of a motor 20 drives two plates 22 and 23 bearing crankshafts 25 and 26 respectively. The crankshaft drives a connecting rod 27 connected to a piston 28 reciprocally moveable in cylinder 29 leading into the chamber 1. The crank 26 drives the connecting rod 30 connected to the piston 31 reciprocally moveable in cylinder 32 leading into the auxiliary chamber 4. This assembly forms a double subsonic control apparatus, the movements of pistons 28 and 31 being simultaneous and in phase with each other.

In this embodiment of the invention the amplitude of the movement of the piston 28 is variable and is measured on a measurement means such as a display device 35. The indications supplied simultaneously by the weighing device 15 and the device 35 are combined and a computer 33 determines the density directly therefrom.

FIGS. 4, 5, and 6 indicate, in a very schematic fashion, an assembly which enables the amplitude of the piston 28 to be varied. The plate 22 has a radial recess 36 in which a threaded rod 37 is guided. One of the ends of the rod 37 is integral with a first angle pinion 38 coacting with a second angle pinion 39 which is integral with an inner shaft 41 journalled in the hollow shaft 21.

As seen in FIG. 5, the crankshaft 25 is integral with a nut 42 which engages the threaded rod 37 and is guided in a radial groove provided in the plate 22.

The motor 20 drives the shaft 21 via a shaft 43 on which a first pinion 44 is fitted which engages a pinion 45 fitted onto the shaft 21.

The differential shaft 43 extends out of both sides of differential 46 which comprises a planetary gear carrier 47 (see FIG. 6) supported by a guide 78 and provided with a manipulable element 79 in front of a graduated scale constituting display device 35.

The planetary gear carrier 47 includes two first planetary gears 48 and 49 which engage two second planetary gears 50 and 51.

A second pinion 52 which drives a pinion 53 is fitted onto a differential shaft 43. The pinion 53 in its turn drives a pinion 54 fitted onto shaft 41.

With this assembly, the shaft 41 and the shaft 21 rotate in one and the same direction at approximately the same velocity and in such a way that the pinion 39 rotates along with pinion 38 without driving it. As the manipulable element 79 is actuated in one direction or the other, the rotational speed of the pinion 39 relative to that of the plate 22 is modified, thus causing the threaded rod 37 to rotate in one direction or the other. The crank 25 thus moves closer to or farther from the center of the plate 22. As a result of this movement, the amplitude of the piston 28 is varied.

By varying the amplitude of the movement of the piston 28 the differential manometer is balanced out. The unknown density is ascertained by introducing both the weight of the patient, measured by the weighing means 15, and the volume, obtained by the equilibration of the differential manometer gauge and indicated on the display device 35 into a computer.

FIG. 2 shows an alternative embodiment in which the crank 25 of the plate 22 is fixed but in which, on the other hand, the crank 26 is mounted in such a way that it can move in a radial direction on the plate 23. Such movement is again associated and displayed by means of the display device 35a. In this diagram the same reference numbers have been used as in FIG. 1 for the same components.

In this embodiment of the invention, the amplitude of the movements of the piston 31 is adjusted to equilibrate the differential monometer gauge. The density is once again determined by introducing both the weight of the patient, measured by the weighing means 15, and the volume, shown on the display device 35a into a computer.

FIG. 3 shows a third embodiment of the invention. In this figure the elements correspond to those of FIGS. 1 and 2 and bear the same reference numbers as in the latter but with the addition of the letter "a". Elements identical to those of the previous embodiments have already been described and need not again be described in detail.

In this third embodiment the auxiliary chamber 4a is itself variable in volume and comprises a base piston 55 which is capable of sliding to a fro. The rod 56 is integral with the base piston at one end and attached to indicator needle 57 moveable along a graduated scale 58.

The device operates in exactly the same manner as the two preceeding embodiments, the volume measurement being obtained by moving the piston 55 until the pressures displayed on the indicator device 9a are equal. In this configuration it is obvious that there will be an equal pressure modulation between the two chambers 1a and 4a when the volume of the chamber 1a less the volume of the body 2a becomes equal to the volume of the chamber 4a, the volume of the body 2a being displayed on the measuring assembly 57,58.

As in the preceeding embodiments, the measured values obtained at 18a and 58 enable the required density to be determined.

With reference to FIGS. 1–3, the following symbols will be adopted:

Vm: the volume of a measuring chamber 1;

Vx: the volume of subject 2 whose density is to be measured;

Vm: the volumetric variation brought about by the piston 28 in the measuring chamber;

Va: the volume of the auxiliary chamber 4, indicated on the scale 58;

$\Delta$Va: the volumetric variation brought about by the piston 31 in the auxiliary chamber and indicated on the scale 58; and P: the atmospheric pressure.

In measuring chamber 1 the subsonic volumetric variation selected has an amplitude of $\Delta$Vm and is applied to a volume Vm−Vx. The amplitude $\Delta$Pm of the subsonic pressure is indicated by the following equation:

$$\frac{\Delta Pm}{P} = \gamma \frac{\Delta Vm}{Vm - Vx}$$

In the above $\gamma$ is the coefficient of adiabatic compressibility.

In chamber 4 the subsonic volumetric variation selected has an amplitude of $\Delta$Va and is applied to the volume Va. The amplitude ΔPa of the subsonic pressure will be as follows:

$$\frac{\Delta Pa}{P} = \gamma \frac{\Delta Va}{Va}$$

The measuring process consists of the equilibration of the subsonic pressures of the two chambers and then reading the device 9 connected to the subsonic differential manometer gauge. This equilibration may be performed by varying the values ΔVm, ΔVa, and/or Va, either alone or in combination while the following conditions of equilibrium are maintained:

$$\frac{\Delta Pm}{P} = \frac{\Delta Pa}{P}$$
$$\frac{\Delta Vm}{Vm - Vx} = \frac{\Delta Va}{Va}$$

Quite remarkably, in this last equation the value of P, like that of $\gamma$ has disappeared, and all the measurements are simply "geometrical" and thus extremely accurate.

This expression may be rewritten more clearly as follows:

$$Vx = Vm - \frac{\Delta Vm}{\Delta Va} Va$$

While it may be possible to construct the main measuring chamber so that its volume could be variable and adjustable, in actual fact, for practical reasons, this chamber will be constructed in a standard size to accomodate a normal sized human being with, at most, the addition of a "childrens'" or even "babies'" model. Vm will thus be a standardized parameter exactly known from the construction of the apparatus and will not be of variable magnitude.

Furthermore, although possible, it appears neither desirable nor necessary, in actual use to utilize variations of ΔVm, ΔVa, and Va simultaneously. Each measurement method has its own advantages. Specifically, the adoption of fixed values for Va and ΔVa and the performance of the measurement by adjusting the value of ΔVm obviously has the advantage of making certain that the subject will be exposed to the same subsonic pressure in all cases. Alternatively, it should be noted that it is only by suitable adjustment of the basis equation for the ratio between Va and ΔVa that the auxiliary chamber and its subsonic control equipment can be miniaturized, which is a considerable technical advantage as all the "accessories" to the measuring chamber can then be accomodated within a reduced space.

The criteria used in selecting a particular subsonic frequency will now be explained.

First the subsonic frequency should be as low as possible. By using such low frequencies an instantaneous pressure can be assumed to directly prevail throughout the measurement chamber at a given moment. Where N is the operating frequency and c is the speed of sound, it is known that the corresponding acoustic wave length λ is defined by the expression λ=c/N.

Thus, where N=5 Hz, c being approximately 300 m/s, λ is 60 meters. Since the distance from the pressure generator to the extreme points of the chamber are on the order of 1 meter, it will be seen that it is perfectly impossible to use acoustic waves of a frequency on the order of 100 Hz, whose corresponding wave length will only be 3 meters.

Other criteria, however, tend to require the adoption of lower and lower frequencies. It is difficult to ensure a perfect hermetic seal in a cabin having a door through which the subject must be able to enter and depart rapidly. Such hermetic seals are not particularly necessary with subsonic frequencies although the acceptable degree of leakage is higher, the higher the frequency adopted. These leakages prove useful in reducing to a minimum any possible thermal effects caused by the fact that the body whose density is being measured is not necessarily at the same temperature as the measuring chamber accommodating it during the measuring operation. For the sake of completeness it may be added that the consequences of thermal phenomena may also be reduced to a minimum by briefly interrupting the measuring operations and equalizing the average pressure between the enclosure and the exterior and by suitable filtration of the indications provided by the differential subsonic pressure gauge. A suitable effective frequency band for the use of the process described is approximately 2-10 Hz.

FIG. 7 schematically illustrates the arrangement of a measuring assembly in accordance with the present invention, each function being illustrated by a symbolic rectangle and the connections between the blocks indicating either the transmission of an item of information or the transmission of an order.

The chamber 1 is illustrated schematically by the rectangle 1, the pressure prevailing therein being P+ΔPm, the auxiliary enclosure is illustrated by the rectangle 4, in which the prevailing pressure is P+ΔPa. The subsonic differential manometer gauge 6 receives these pressures through conduits 60 and 61. Its measurement reading is proportional to the differences between ΔPm and ΔPa and is transmitted via the cable 62 to the discriminator 63 which processes and issues re-equilibration orders, based on ΔVm, via the cable 64, or based upon ΔVa or Va, via the cable 65, in such a manner as to re-equilibrate the subsonic differential manometer gauge 6 by changing the previously referred to settings.

The information of the settings of the controls of ΔVm or ΔVa or Va which lead to equilibrium pressure, are transmitted to a computer 68 via the cables 66 and 67 respectively. This computer 68 also receives, via a cable 70, the information as to the weight of the subject which is processed by the weighing device shown at 15. Finally, the computer 68 determines the density and transmits this value to the indicator 71 via the cable 72.

The invention is not limited only to those embodiments specifically described and illustrated by way of example and numerous modifications, additions and substitutions may be made for the means specifically disclosed without thereby departing from the scope of the invention.

What is claimed is:

1. An apparatus for measuring the density of a body which comprises:
   (a) a main chamber adapted to receive the body whose density is to be measured;
   (b) an auxiliary chamber;
   (c) a subsonic wave generator for subjecting both of said chambers, in phase, to amplitude variations of pressure so as to generate subsonic waves;
   (d) a differential manometer arranged between each of said chambers;

(e) means for equalizing the subsonic pressures of said two chambers;

(f) measurement means driven by said means for equalizing said subsonic pressures; and (g) weighing means for weighing said body, said weighing means being arranged within said main chamber.

2. The apparatus as defined by claim 1 further comprising means connected to said measurement means and to said weighing means, for receiving data from each of these means and adapted to utilize said data to calculate the density of said body.

3. The apparatus as defined by claim 1 wherein said subsonic wave generator generates said subsonic waves in each of said chambers by volumetric displacement, and said means for equalizing said subsonic pressures in each of said chambers comprises means for modifying the amplitude of the volumetric displacement generating said subsonic waves in said chamber.

4. The apparatus as defined by claim 3 wherein said subsonic wave generator comprises two assemblies, each of said assemblies being driven by a motor, and
(a) a shaft connected to said motor;
(b) a piston arranged within a cylinder communicating with each of said chambers so as to reciprocate in said cylinder;
(c) a crankshaft connected to said piston; and
(d) means for varying the amplitude of reciprocation by said piston reciprocating in the cylinder communicating with said main chamber.

5. The apparatus as defined by claim 4 further comprising a plate arranged between said crankshaft and a hollow shaft, operatively connected to said hollow shaft so as to be driven thereby.

6. The apparatus as defined by claim 5 wherein an inner shaft is inserted within said hollow shaft, said inner shaft ending in a first angle pinion, said apparatus further comprising: a threaded rod radially arranged within said plate, said threaded rod ending in a second angle pinion arranged to engage said first angle pinion, said crankshaft ending in a nut which in turn threadably engages said threaded rod; and a connecting rod arranged between said crankshaft and said piston, said connecting rod being adapted to raise and lower said piston as said plate is rotated by said hollow shaft.

7. The apparatus as defined by claim 6 further comprising a differential operatively associated with said hollow shaft and said inner shaft.

8. The apparatus as defined by claim 7 wherein said differential comprises a guide; a planetary gear carrier within said guide; two first planetary gears radially arranged within said planetary gear carrier; a differential shaft extending out of said differential and comprising a first pinion adapted to drive said hollow shaft and a second pinion adapted to drive said inner shaft on opposite sides of said differential, said first and second pinions being adapted to be rotated in opposite directions when the side of said differential shaft comprising said second pinion is driven by said motor thus causing said hollow shaft and said inner shaft to rotate at the same rotational velocity.

9. The apparatus as defined by claim 8 wherein said measuring means is operatively connected to said differential, and wherein said measuring means comprises a manipulable element attached to said planetary gear carrier such that both of said opposite sides of said differential shaft are driven in the same direction as said manipulable element is rotatably moved thus causing said hollow shaft and said inner shaft to rotate at different velocities relative to one another which in turn causes said second angle pinion to rotate said threaded rod thus altering the radial position of said crankshaft as said nut moves along said threaded rod.

10. The apparatus as defined by claim 1 wherein said subsonic wave generator generates said subsonic waves in each of said chambers by volumetric displacement, said means for equalizing said subsonic pressures in each of said chambers comprising means for modifying the amplitude of the volumetric displacement generating said subsonic waves in said auxiliary chamber.

11. The apparatus as defined by claim 10 wherein said subsonic wave generator comprises two assemblies, each of said assemblies being driven by a motor, and
(a) a shaft connected to said motor;
(b) a piston arranged within a cylinder communicating with each of said chambers so as to reciprocate in said cylinder;
(c) a crankshaft connected to said piston; and
(d) means for varying the amplitude of reciprocation by said piston reciprocating in the cylinder communicating with said auxiliary chamber.

12. The apparatus as defined by claim 11 further comprising a plate arranged between said crankshaft and a hollow shaft, operatively connected to said hollow shaft so as to be driven thereby.

13. The apparatus as defined by claim 12 wherein an inner shaft is inserted within said hollow shaft, said inner shaft ending in a first angle pinion, said apparatus further comprising: a threaded rod radially arranged within said plate, said threaded rod ending in a second angle pinion arranged to engage said first angle pinion, said crankshaft ending in a nut which threadably engages said threaded rod; and a connecting rod being adapted to raise and lower said piston as said plate is rotated by said hollow shaft.

14. The apparatus as defined by claim 13 further comprising a differential operatively associated with said hollow shaft and said inner shaft.

15. The apparatus as defined by claim 14 wherein said differential comprises a guide; a planetary gear carrier within said guide; two first planetary gears radially arranged within said planetary gear carrier; a differential shaft extending out of said differential and comprising a first pinion adapted to drive said hollow shaft and a second pinion adapted to drive said inner shaft on opposite sides of said differential, said first and second pinions being adapted to be rotated in opposite directions when the side of said shaft comprising said second pinion is driven by said motor thus causing said hollow shaft and said inner shaft to rotate at the same rotational velocity.

16. The apparatus as defined by claim 15 wherein said measuring means is operatively connected to said differential, and wherein said measuring means comprises a manipulable element attached to said planetary gear carrier such that both of said opposite sides of said differential shaft are driven in the same direction as said manipulable element is rotatably moved thus causing said hollow shaft and said inner shaft to rotate at different velocities relative to one another which in turn causes said second angle pinion to rotate said threaded rod thus altering the radial position of said crankshaft as said nut moves along said threaded rod.

17. The apparatus as defined by claim 1 wherein said means for equalizing the subsonic pressures of said two chambers comprises means for varying the volume of said auxiliary chamber.

18. The apparatus as defined by claim 17 wherein said subsonic wave generator generates said subsonic waves in each of said chambers by volumetric displacement, and said means for equalizing said subsonic pressures in each of said chambers comprises means for modifying the volume of said auxiliary chamber.

19. The apparatus as defined by claim 18 wherein said means for modifying the volume of said auxiliary chamber comprises a base reciprocable piston adapted to vary the volume of said auxiliary chamber.

20. The apparatus as defined by claim 1 wherein said means for equalizing the subsonic pressures between each of said chambers comprises a discriminator operatively connected to said differential manometer for processing information received from said differential manometer and in turn formulating instructions for equilibrating the subsonic pressures between each of said chambers based upon said information, said apparatus further comprising computer means for receiving data from said measurement means and information generated by said weighing means and for calculating the density of said body based upon said data and information.

21. The apparatus as defined by claim 20 wherein said computer means further comprises display means for displaying the density calculated by said computer means.

* * * * *

UNITED STATES PATENT AND TRADEMARK OFFICE
CERTIFICATE OF CORRECTION

PATENT NO. : 4,184,371
DATED : January 22, 1980
INVENTOR(S) : Roland BRACHET

It is certified that error appears in the above-identified patent and that said Letters Patent are hereby corrected as shown below:

At column 3, line 66, "breath" should read ---breathe---;
At column 6, line 11, "monometer" should read ---manometer---;
At column 6, line 26, "a" should read ---and---;
At column 6, line 40, "precceding" should read ---preceding---;
At column 6, line 48, "Vm" should read ---$\Delta$Vm---;
At column 7, line 34, "childrens" should read ---children's---.

Signed and Sealed this

Sixth Day of May 1980

[SEAL]

*Attest:*

SIDNEY A. DIAMOND

*Attesting Officer*

*Commissioner of Patents and Trademarks*